US006254892B1

(12) United States Patent
Duccini et al.

(10) Patent No.: US 6,254,892 B1
(45) Date of Patent: Jul. 3, 2001

(54) PELLET FORMULATIONS

(75) Inventors: Yves Duccini, Beauvais; Johan Tatin, Compiegne; Francois Gauthier, Verneuil en Halatte, all of (FR)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/507,852

(22) Filed: Feb. 22, 2000

(51) Int. Cl.$^7$ .............................. A61K 9/16; A61K 9/14; A61K 47/32

(52) U.S. Cl. .................... 424/497; 424/489; 424/488; 514/772.4

(58) Field of Search ................................ 424/451, 489, 424/497, 488; 514/772.4

(56) References Cited

U.S. PATENT DOCUMENTS

| | | |
|---|---|---|
| 4,372,868 | 2/1983 | Saran et al. . |
| 4,695,397 | 9/1987 | Sommer et al. . |
| 5,229,131 | * 7/1993 | Amidon et al. ............... 424/451 |

FOREIGN PATENT DOCUMENTS

| | | |
|---|---|---|
| 37026 | 10/1981 | (EP) . |
| 75818 | 4/1983 | (EP) . |
| 238341 | 9/1987 | (EP) . |
| 481547 | 4/1992 | (EP) . |
| 522766 | 1/1993 | (EP) . |
| 799886 | 10/1997 | (EP) . |
| 972825 | * 1/2000 | (EP) . |

OTHER PUBLICATIONS

Journal of Pharmaceutical Sciences, vol. 61, No. 11, pp. 1695–1711 (1972).

* cited by examiner

Primary Examiner—Thurman K. Page
Assistant Examiner—Blessing Fubara
(74) Attorney, Agent, or Firm—Thomas J. Howell

(57) ABSTRACT

The invention concerns chemical compositions in the form of pellets which disintegrate quickly and efficiently in aqueous media and a method of producing the pellets. Such pellets comprise (a) at least one constituent with pharmaceutical, agrochemical, water treatment, water softening, fabric softening or detergency activity; (b) at least one disintegration agent comprising one or more crosslinked polyacrylate water absorbent polymers with a gel-formation time of 30 seconds or less and (c) at least one water transport agent to transport water into the pellet when the pellet contacts water.

15 Claims, No Drawings

PELLET FORMULATIONS

The present invention relates to improved chemical compositions in pellet form which disintegrate quickly and efficiently in aqueous media. By "pellet", we mean any solid formulation, including, but not limited to, tablets, bricks, bars, granules, balls, or blocks, also agglomerated materials such as those which form as a result of material sticking together during storage, especially under high humidity conditions.

It is well known to use chemical compositions in pellet form, for example, in the field of medicine and agriculture and more recently other areas such as in detergent applications. Pellets offer certain advantages over granular compositions; they are non-dusting, do not require measuring, take less space because they are compressed and the ingredients do not segregate during transit and storage. However, problems are experienced regarding the dissolution or disintegration of the pellets in use. In the manufacturing process, a balance must be kept between a pellet pressure which is, on the one hand, high enough to ensure that the pellets are well formed and resistant to handling, and a pellet pressure which is, on the other hand, low enough to achieve an appropriate solubility/dispersibility profile. To combat this problem, it is known to be helpful to use a processing additive either to improve pellet cohesion without the use of high pelleting pressure or to improve tablet dispersibility.

Looking specifically at additives which improve dispersibility, Journal of Pharmaceutical Sciences Vol. 61, No., 11, 1972, pp 1695–1711 reviews the various classes of known disintegrants; for example, materials which, (i) cause disintegration by evolving gas, such as sodium bicarbonate in the presence of citric or tartaric acid; (ii) those which promote water absorption, such as starch, colloidal silicon dioxide, carboxymethyl cellulose and rice starch; (iii) those which swell, for example, crosslinked polyacrylic acids, crosslinked gum arabic, carboxymethyl cellulose; (iv) those which increase porosity such as potato and corn starch and finally (v) those which undergo physicochemical bonding, such as micro crystalline cellulose and kaolin.

There are also many prior art patent documents directed to detergent tablets which contain disintegration agents. Examples of these include: EP-A-0799886 which discloses the use of starch derivatives, cellulose compounds, polyvinyl pyrrolidone compounds, bentonite compounds, alginates, gelatine and pectines as disintegrants and EP-A-0522766 which lists corn, maize, rice and potato starches, and starch derivatives, cellulose and cellulose derivatives and various synthetic organic polymers such as polyethylene glycol, crosslinked polyvinyl pyrrolidone and inorganic materials which swell such as bentonite clay, as disintegrants.

EP-A-0481547 teaches multilayer machine dishwashing detergent tablets which contain an outer layer, a barrier layer and an inner layer. The tablets release the detergent ingredients sequentially, first from the outer layer and then from the inner layer and the time delay between the two dissolutions is controlled by the thickness and choice of ingredients in the barrier layer separating the outer and inner layers. One of the ingredients in this barrier layer is a disintegrant which preferably includes one of a maleic acid/acrylic acid copolymer or a salt thereof, ethylene maleic anhydride crosslinked polymer and polyethylene glycol.

EP-A-0238341 identifies sequestering agents, for instance, nitrilo triacetic acid or diethylene diamine tetra acetic acid or a low molecular weight anionic polymer formed from ethylenically unsaturated monomers, e.g., unsaturated carboxylic acid, sulphonic acid or phosphonic acid monomers, as disintegrants. Further, this document mentions, when discussing the teaching of background art documents EP-A-0075818 and EP-A-0037026, that the conventional insoluble water swellable disintegration aids disclosed therein, such as high molecular carbohydrates like starch, pulverised cellulose such as ground wood, or polyvinyl pyrrolidone and so on, either do not lead to satisfactory disintegration or the disintegration is very slow at low temperatures. Another disadvantage observed through the use of cellulose and cellulose derivatives is that at use levels which are effective to promote disintegration, for example around 5% by weight of the tablet, the tablets are friable and break easily. This problem can be overcome by the addition of processing aids, for example binders which "glue" the tablet particles together, but this adds cost and reduces the volume of the tablet which is available for active ingredients.

The dissolution or disintegration of tablets for use in detergent compositions for automatic dishwashing is usually controlled to ensure dissolution which is regular but not too quick so as to avoid too much of the detergent composition being consumed in the pre-wash. However, during the main dishwash cycle it is advantageous for the remainder of the tablet to dissolve quickly so that residual tablet solids are not a problem on the dishware. By contrast, a key requirement in detergent compositions for laundry applications is to deliver as much of the detergent composition as possible so that it is available in the initial step of the wash. This will also be the case if the dishwashing machine has no pre-wash cycle. Since calcium and magnesium hardness ions in the wash water are already present at the beginning of the wash cycle, there is a high risk that sequestering ingredients are at too low a concentration and these will precipitate together with these hardness ions. This will result in insoluble scale being formed on the garments being laundered and a reduced amount of active material in the detergent composition being available for cleaning. With certain builders in detergent compositions, for example, sodium tripolyphosphate (STPP), this problem is critical since Ca/STPP precipitates can form scale which is very difficult to remove. The size of the tablets and the application conditions will also affect the tablet dispersability profile; for example, tablets for use in laundry applications are typically considerably larger than those used in automatic dishwashing machines or in water softening; 40 gram (g) up to 55 g tablets for laundry versus 20–25 g tablets for dishwashing and water softening. This fact, coupled with the tendency for the laundry tablet to be buried in the garments being washed means that the solubility requirements are particularly difficult to meet for tablets used in laundry applications as compared to other applications.

The applicants have previously disclosed, in French patent application 9807643, pellet formulations which disintegrate or dissolve very quickly on contact with water, making them suitable for use in applications which require the active ingredients to be delivered quickly. These pellets comprise: (a) at least one constituent with pharmaceutical, agrochemical, water treatment, water softening, fabric softening or detergency activity; and (b) at least one disintegration agent comprising one or more crosslinked polyacrylate water absorbent polymers with a gel-formation time of 30 seconds or less.

Such pellets have sufficient strength so that they do not crumble or break whilst being stored, transported or handled and are able to be stored under various climatic conditions involving fluctuating temperatures and humidities. It is particularly desirable that the pellets are sensitive to water but not to moisture. They must also have good activity, which requires a high content of active ingredients, and be able to exert this good activity at different temperatures and over a wide spectrum of application conditions, for example over a range of degrees of water hardness in the case of detergents.

The applicants have now found that these pellets can be even further optimised. It has been observed by the applicants that the rate of tablet disintegration is increased with increasing levels of disintegration agent present in the tablet, however, when the tablet contains these disintegration agents in, for example, amounts of 2% or more by weight, a gel forms when the tablet comes into contact with water and this prevents penetration of the water into the centre of the tablet, i.e. this gel retards the disintegration.

The aim of the present invention, therefore, is to provide pellet formulations which have further improved rates of disintegration and which overcome the difficulties caused by gel formation.

Accordingly, the present invention provides a chemical composition in pellet form comprising: (a) at least one constituent with pharmaceutical, agrochemical, water softening, fabric softening or detergency activity; (b) at least one disintegration agent comprising one or more crosslinked polyacrylate water absorbent polymers with a gel-formation time of 30 seconds or less; and (c) at least one water transport agent to transport water into the pellet when the pellet contacts water.

The purpose of the water transport agent is to entrain water quickly into the center of the pellet so that the crosslinked polyacrylate water absorbent polymer within the tablet can be caused to swell and thereby facilitate fast disintegration of the pellet. Without such water transport agents the water absorbent polymer close to the surface of the pellet will swell on contact with water and, if the polymers are at a concentration of, for example, 2% or more by weight of the pellet, they will form a gel which will effectively prevent further water penetration into the pellet. The preferred water transport agents comprise one or more of amorphous cellulose, microcrystalline cellulose, modified cellulose and synthetic hollow fibres. A fine particle size for the water transport agent is advantageous, for example, 200 µm or less and preferably 80 µm or less.

The amount of crosslinked polyacrylate water absorbent polymer (disintegration agent) is generally from 0.5 to 2.0% by weight of the pellet formulation, and preferably from 1.0 to 1.5% by weight, also the amount of water transport agent can be from 0.5 to 5.0% by weight of the pellet formulation, preferably from 2.0 to 3% by weight. A particularly favourable composition comprises 1.0% by weight of the pellet of crosslinked polyacrylate water absorbent polymer and 2.0% by weight of a microcrystalline cellulose.

It is particularly advantageous for the crosslinked polyacrylate water absorbent polymers to have a gel-formation time of 10 seconds or less.

In a further embodiment of the present invention, the rate of disintegration of the pellet can be still further increased by modifying the disintegration agent by spraying it with water prior to incorporating it into the pellet. The quantity of water may be from 5–50% weight/weight (w/w) and is preferably from 5–20% w/w.

The present invention is also directed to a method of improving the speed of disintegration of chemical compositions in pellet form by incorporating therein:
(a) at least one constituent with pharmaceutical, agrochemical, water treatment, water softening, fabric softening or detergency activity;
(b) at least one disintegration agent comprising one or more crosslinked polyacrylate water absorbent polymers with a gel formation time of 30 seconds or less; and
(c) at least one water transport agent to transport water into the pellet when the pellet contacts water.

By "improving the speed of disintegration", it is meant that the time of disintegration is less for pellets according to the present invention as compared with pellets which do not contain a mixture of one or more crosslinked polyacrylate water absorbent polymers with a gel formation time of 30 seconds or less and a water transport agent.

The crosslinked polyacrylate water absorbent polymers used in the present invention are typically those resulting from the radical polymerisation and crosslinking of, at least one water soluble ethylenically unsaturated monomer selected from: (meth)acrylic acid, alkali metal or ammonium salts of (meth)acrylic acid, (meth)acrylic acid esters, maleic acid, maleic anhydride and (meth)acrylamide.

The crosslinking reaction may be carried out using at least one of the following three methods:
(i) crosslinking by radical polymerisation with a co-monomer comprising at least two double bonds. Examples of such co-monomers include: trimethylol propane di(tri)(meth)acrylate, N,N-methylene bis (methyl)acrylamide, glyoxal bisacrylamide, ethylene glycol di(meth)acrylate;
(ii) crosslinking by radical copolymerisation with a so-called functional monomer comprising one double bond (active in copolymerisation) and, at least one functional group capable of leading to crosslinking reactions between a functional group and a chemically active moiety of the main water soluble monomer(s). Examples of this type of crosslinker include: N-methylol(meth)-acrylamide, and glycidyl(meth) acrylate; and
(iii) crosslinking by adding a non-polymerisable functional crosslinker containing at least two functional groups capable of reacting with the chemically active moieties of the water soluble monomer(s). Examples of this type of crosslinker include: glyoxal, ethylene glycol, (poly)ethylene glycol diglycidyl ether, (poly) propylene glycol diglycidyl ether, (di)glycerol polyglycidyl ether, polyglycerol polyglycidyl ether, epichlorohydrin, ethylene diamine and zinc acetate.

The amount of crosslinker necessary for the production of the water-absorbing polymers is typically in the range of 0.001 and 10 weight percent most preferably in the range of 0.01 and 5 weight percent, based upon the total weight of water-soluble ethylenic unsaturated monomer(s).

The crosslinked polyacrylate water absorbent polymers used in the present invention may be produced by any suitable radical polymerisation method. The solution-type polymerisation processes (also called gel processes) most commonly employed are those disclosed in EP-A-0530438, a and a typical reversed-phase suspension polymerisation process is such as that described in EP-A-0258120. The essential feature of the crosslinked polyacrylate water absorbent polymers used in the present invention is that they have a gel-formation time of less than 30 seconds.

In addition to the composition comprising at least one constituent with pharmaceutical, agrochemical, water treatment, water softening, fabric softening or detergency activity, the composition may also comprise other ingredients including, for example, one or more of the following: processing additives, adjuvants, coatings materials, enzymes, builders, scale inhibitors, emulsifiers, surfactants, soaps, dispersants, zeolites, de-greasing agents, anti-foaming agents, phosphates, phosphonates, carbonates, bicarbonates, citrate, citric acid, organic chelants, bleach, optical brighteners, fillers, extenders, soil removers, deflocculating agents, anti-coagulants, anti-drift agents, diluents, and carriers.

The present invention will now be described with reference to the following Examples.

The test procedures used are intended to simulate a real application. Detergent tablets using a typical laundry detergent composition were made using conventional tablet making equipment. Test tablets were loaded with both a disintegration agent and a water transport agent, and the disintegration efficiency of these test tablets was then tested and compared against similar control tablets loaded with either, only a disintegration agent, or only a water transportation agent or without either a disintegration agent or a water transport agent. The laundry detergent composition used is detailed in Table 1 below:

TABLE 1

| Ingredients | Detergent Composition |
| --- | --- |
| Anionic Surfactant | 5–15% |
| Non-ionic Surfactant | 5–15% |
| Soap | <5% |
| Zeolite | >30% |
| polymer builder | <5% |
| Phosphonate | <5% |
| Bleach | 5–15% |

The disintegration agent tested was a crosslinked polyacrylate water absorbent polymer with a gel formation time of 5 seconds. This material is available from Norso Haas SA (France).

The gel formation time of the disintegration agent was measured using the following method, often referred to in the art as the vortex test or vortex swelling rate test.

An aqueous solution of sodium chloride is prepared by dissolving analytical grade sodium chloride in demineralized water up to a 0.9% weight concentration of salt in the final solution. This 0.9% wt. sodium chloride aqueous solution is a reference test liquid ("test liquid") commonly used in the characterisation of water absorbing polymers. In a temperature controlled room (20° C.), the crosslinked polyacrylate water absorbing polymer (3 g) is introduced into a beaker (200 ml) of internal diameter (55 mm). The beaker is placed over an electromagnetic stirrer and a magnetic bar (45 mm X 8 mm) is introduced into it for stirring. The stirring speed is fixed at 600+/−20 rpm and the beaker is rapidly charged with the test liquid (100 g). As soon as addition of the test liquid is complete, this is counted as time zero and the point from which time is measured. Time measurements are stopped when the stirring vortex has disappeared due to the formation of a gel by the water-absorbing polymer. For extremely fast gelling polymers, it may be necessary to invert the order of addition of the polymer and test liquid to the beaker.

The rate of disintegration of the test and control tablets was determined using the following test method.

Test and control tablets containing the detergent composition given in Table 1 were prepared using conventional tablet making apparatus. A measure of the rate of disintegration for each tablet was measured as follows. Cold tap water (4.5 litres) at a temperature of 16–170° C. was placed in a 5 litre beaker on a support, and a pre-weighed tablet was added. The solution was then agitated at 400 rpm for either 10 or 5 minutes using a magnetic bar and magnetic bar stirring apparatus. At the end of the test cycle, the residue was placed in a cup, oven dried at 80° C. for 2 hours and re-weighed. The percentage residue was calculated as follows:

Weight of residue×100/Weight of tablet at the start

The results of the tests are presented in Table 2 below:

TABLE 2

Percentage of tablet remaining

| Example | Additive | | Comments |
| --- | --- | --- | --- |
| | | % Residue after 10 minutes | |
| 1 | None (control) | 61 | Tablet difficult to dissolve |
| 2 | 1.5% disintegration agent (control) | 33 | Moderate rate of disintegration |
| 3 | 3% water transport agent (control) | 47 | Moderate rate of disintegration |
| 4 | 5% water transport agent (control) | 2 | Fragile tablet |
| 5 | 1% disintegration agent + 1% water transport agent (experimental test) | 29 | Excellent tablet, good rate of disintegration |
| 6 | 1% disintegration agent + 2% water transport agent (experimental test) | 18 | Excellent tablet, fast rate of disintegration |
| 7 | 1% disintegration agent + 3% water transport agent (experimental test) | 0 | Excellent tablet and excellent rate of disintegration |
| | | % Residue after 5 mins | |
| 8 | 5% water transport agent (control) | 56 | Fragile tablet |
| 9 | 1% disintegration agent* + 2% water transport agent (experimental test) | 26 | Excellent tablet, and excellent rate of disintegration |

*Indicates that the disintegration agent was modified prior to incorporation into the tablet by spraying it with 20% w/w of deionised water As demonstrated by these results, tablets comprising a combination of a disintegration and a water transport agent, examples 5–6, produce excellent tablets and disintegrate much quicker than tablets which only comprise one of these two ingredients.

Furthermore, when the disintegration agent is treated with 20% w/w deionised water, example 9, the rate of disintegration is still further increased.

We claim:

1. A chemical composition in pellet form comprising:
    (a) at least one constituent with pharmaceutical, agrochemical, water treatment, water softening, fabric softening or detergency activity;
    (b) at least one disintegration agent comprising one or more cross-linked polyacrylate water absorbent polymers with a gel formation time of 30 seconds or less; and
    (c) at least one water entraining agent transporting water to a pellet core when the pellet contacts water; wherein the water entraining agent is incorporated in a mixture with the active constituent (a) and the disintegration agent (b).

2. A chemical composition according to claim 1 wherein the water entraining agent is selected from one or more the group consisting of amorphous cellulose, microcrystalline cellulose and synthetic hollow fibres.

3. A chemical composition according to claim 1 wherein the disintegration agent is prepared from the radical polymerization and cross-linking of at least one water soluble ethylenically unsaturated monomer selected from the group consisting of (meth)acrylic acid, alkali metal or ammonium salts of (meth)acrylic acid, (meth)acrylic acid esters, maleic acid, maleic anhydride and (metb)acrylamide.

4. A chemical composition according to claim 1 wherein the amount of disintegration agent, based on pellet composition weight percent, is from 0.5 to 2.0% and wherein the amount of water entraining agent is from 0.5 to 5.0%.

5. A chemical composition according to claim 1 wherein the disintegration agent is treated with water prior to formation of the pellet.

6. A method of improving the speed of disintegration of a chemical composition in pellet form comprising a step of incorporating together in a mixture:

(a) at least one constituent with pharmaceutical, agrochemical, water treatment, water softening, fabric softening or detergency activity;

(b) at least one disintegration agent comprising one or more cross-linked polyacrylate water absorbent polymers with a gel formation time of 30 seconds or less; and (c) at least one water entraining agent transporting water to a pellet core when the pellet contacts water.

7. A method according to claim 6 wherein the water entraining agent is selected from one or more the group consisting of amorphous cellulose, microcrystalline cellulose and synthetic hollow fibres.

8. A method according to claim 6 wherein the disintegration agent is prepared from the radical polymerization and cross-linking of at least one water soluble ethylenically unsaturated monomer selected from the group consisting of (meth)acrylic acid, alkali metal or ammonium salts of (meth)acrylic acid, (meth)acrylic acid esters, maleic acid, maleic anhydride and (meth)acrylamide.

9. A method according to claim 6 wherein the amount of disintegration agent, based on pellet composition weight percent, is from 0.5 to 2.0% and wherein the amount of water entraining agent is from 0.5 to 5.0%.

10. A method according to claim 6 wherein the disintegration agent is treated with water prior to formation of the pellet.

11. Chemical composition according to claim 1 wherein the gel-formation time of the disintegration agent is 10 seconds or less.

12. Chemical composition according to claim 1 wherein the pellet form is a solid formulation selected from tablets, bricks, bars, granules, balls, blocks and agglomerated materials.

13. Chemical composition according to claim 2 wherein the disintegration agent results from the radical polymerisation and crosslinking of at least one water soluble ethylenically unsaturated monomer selected from: (meth)acrylic acid, alkali metal or ammonium salts of (meth)acrylic acid, (meth)acrylic acid esters, maleic acid, maleic anhydride and (meth)acrylamide.

14. Method according to claim 6 wherein the gel-formation time is 10 seconds or less.

15. Method according to claim 6 wherein the pellet is a solid formulation selected from tablets, bricks, bars, granules, balls, blocks and agglomerated materials.

* * * * *